United States Patent
Trautman et al.

(10) Patent No.: US 7,087,035 B2
(45) Date of Patent: Aug. 8, 2006

(54) DEVICE AND METHOD FOR ENHANCING SKIN PIERCING BY MICROPROTRUSIONS

(75) Inventors: Joseph C. Trautman, Sunnyvale, CA (US); Michel J. N. Cormier, Mountain View, CA (US); Kellee Eng, Gilroy, CA (US); Wei-Qi Lin, Palo Alto, CA (US); Hyunok L. Kim, Walnut, CA (US); Sara L. Sendelbeck, Palo, CA (US); Armand P. Neukermans, Portola Valley, CA (US); Bruce P. Edwards, Palo Alto, CA (US); Wai-Loong Lim, Menlo Park, CA (US); Andrew I. Poutiatine, Menlo Park, CA (US); J. Richard Gyory, North Oaks, MN (US)

(73) Assignee: Alza Corporation, Mountain View, CA (US)

( * ) Notice: Subject to any disclaimer, the term of this patent is extended or adjusted under 35 U.S.C. 154(b) by 459 days.

(21) Appl. No.: 09/733,506

(22) Filed: Dec. 8, 2000

(65) Prior Publication Data

US 2002/0032415 A1 Mar. 14, 2002

Related U.S. Application Data

(60) Provisional application No. 60/216,877, filed on Jul. 7, 2000, and provisional application No. 60/172,703, filed on Dec. 10, 1999.

(51) Int. Cl.
*A61B 17/20* (2006.01)
*A61B 17/22* (2006.01)

(52) U.S. Cl. ................ 604/22; 604/20; 604/892.1; 604/132; 604/68

(58) Field of Classification Search .......... 604/65, 604/132, 68, 20, 890.1, 892.1, 46, 501, 22, 604/272
See application file for complete search history.

(56) References Cited

U.S. PATENT DOCUMENTS

| RE25,637 E | 9/1964 | Kravitz et al. ............. 128/253 |
| 3,814,097 A | 6/1974 | Ganderston et al. ........ 128/268 |
| 3,964,482 A | 6/1976 | Gerstel et al. ............. 128/260 |
| 4,340,480 A | 7/1982 | Pall et al. .................. 210/490 |
| 4,379,454 A | 4/1983 | Campbell et al. .......... 604/897 |
| 4,588,580 A | 5/1986 | Gale et al. .................. 424/21 |
| 4,655,766 A | 4/1987 | Theeuwes et al. ......... 604/896 |
| 4,698,062 A | 10/1987 | Gale et al. ................. 604/896 |

(Continued)

FOREIGN PATENT DOCUMENTS

| AT | 397 466 B | 9/1993 |
| EP | 0 132 940 | 2/1985 |
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO 99/29365 | 6/1999 |
| WO | WO 00/74763 | 12/2000 |

*Primary Examiner*—Henry Bennett

(57) ABSTRACT

A device and method for enhancing skin piercing by microprotrusions involves pre-stretching the skin to enhance pathway formation when the microprotrusions are pressed into the skin. An expandable device includes skin engaging opposite ends that contact the skin surface so that when the device is expanded the skin is stretched. The skin is placed under a tension of about 0.01 to about 10 megapascals, preferably about 0.05 to 2 megapascals. The device has a plurality of microprotrusions which penetrate the skin while the skin is being stretched by the expanded device. Another stretching device employs suction for skin stretching.

12 Claims, 13 Drawing Sheets

U.S. PATENT DOCUMENTS

| | | | |
|---|---|---|---|
| 4,753,651 A | 6/1988 | Eckenhoff | 424/449 |
| 4,832,953 A | 5/1989 | Campbell et al. | 424/448 |
| 4,867,982 A | 9/1989 | Campbell et al. | 424/449 |
| 5,080,646 A | 1/1992 | Theeuwes et al. | 604/20 |
| 5,147,296 A | 9/1992 | Theeuwes et al. | 604/20 |
| 5,169,382 A | 12/1992 | Theeuwes et al. | 604/20 |
| 5,169,383 A | 12/1992 | Gyory et al. | 604/20 |
| 5,242,406 A | 9/1993 | Gross et al. | 604/132 |
| 5,250,023 A | 10/1993 | Lee et al. | 604/20 |
| 5,268,209 A | 12/1993 | Hunt et al. | 428/34.3 |
| 5,279,544 A | 1/1994 | Gross et al. | 604/20 |
| 5,310,404 A | 5/1994 | Gyory et al. | 604/20 |
| 5,312,456 A | 5/1994 | Reed et al. | 411/456 |
| 5,385,543 A | 1/1995 | Haak et al. | 604/20 |
| 5,423,739 A | 6/1995 | Phipps et al. | 604/20 |

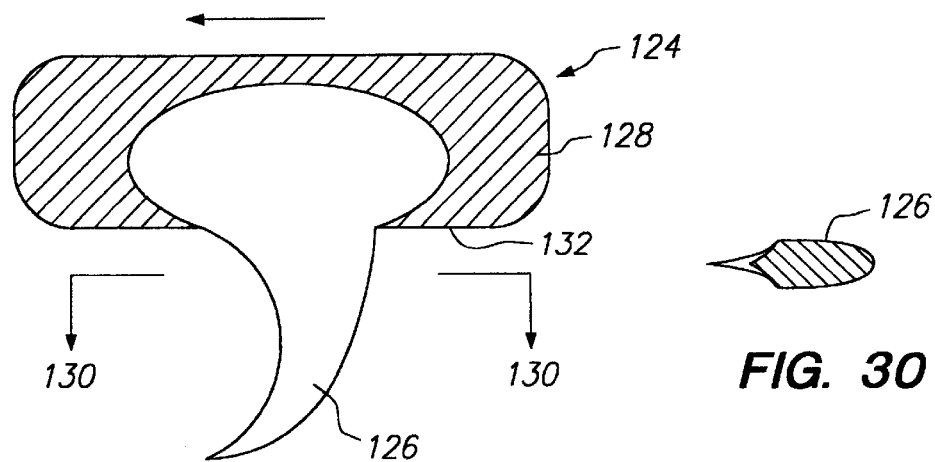
FIG. 29
FIG. 30
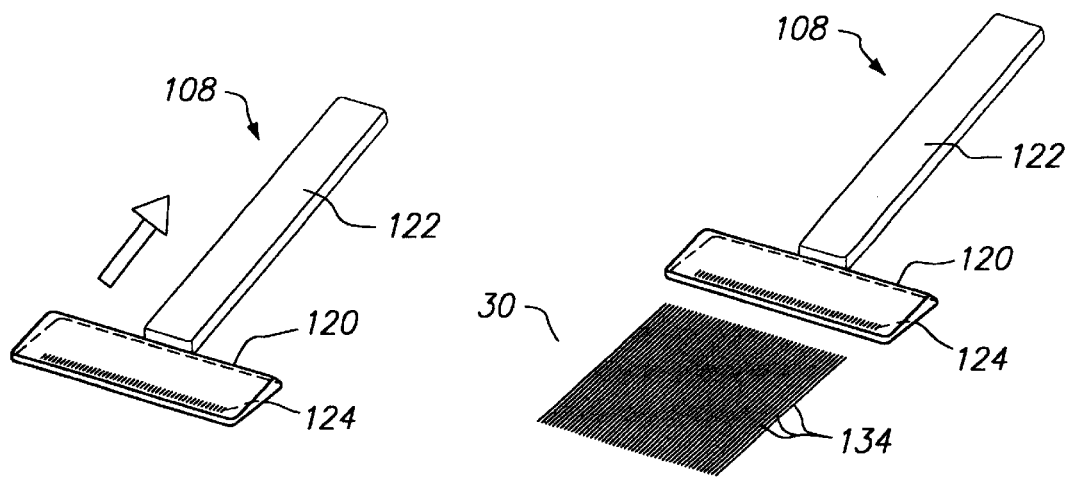
FIG. 31
FIG. 32

DEVICE AND METHOD FOR ENHANCING SKIN PIERCING BY MICROPROTRUSIONS

CROSS REFERENCE TO RELATED APPLICATIONS

This application claims benefit under 35 USC §119(e) to U.S. Provisional Patent Applications 60/172,703 filed Dec. 10, 1999, and 60/216,877 filed Jul. 7, 2000.

TECHNICAL FIELD

The present invention relates to transdermal agent delivery and more particularly, to the transdermal delivery of macromolecular agents such as polypeptides, proteins, oligonucleotides and polysaccharides. The present invention relates to devices which have microprotrusions to pierce the outermost layer of a body surface (e.g., the skin) to enhance the transdermal flux of the agents during transdermal delivery.

BACKGROUND ART

Interest in the percutaneous or transdermal delivery of peptides, proteins, and other macromolecules, such as oligonucleotides, to the human body continues to grow with the increasing number of medically useful peptides and proteins becoming available in large quantities and pure form. The transdermal delivery of peptides and proteins still faces significant problems. In many instances, the rate of delivery or flux of polypeptides through the skin is insufficient to produce a desired therapeutic effect due to the low transdermal permeability coefficient of macromolecules and the binding of the polypeptides to the skin. In addition, polypeptides and proteins are easily degraded during and after penetration into the skin, prior to reaching target cells. Likewise, the passive transdermal flux of many low molecular weight compounds is too limited to be therapeutically effective.

One method of increasing the transdermal delivery of agents relies on the application of an electric current across the body surface referred to as "electrotransport." "Electrotransport" refers generally to the passage of a beneficial agent, e.g., a drug or drug precursor, through a body surface, such as skin, mucous membranes, nails, and the like. The transport of the agent is induced or enhanced by the application of an electrical potential, which results in the application of electric current, which delivers or enhances delivery of the agent. The electrotransport of agents through a body surface may be attained in various manners. One widely used electrotransport process, iontophoresis involves the electrically induced transport of charged ions. Electroosmosis, another type of electrotransport process, involves the movement of a solvent with the agent through a membrane under the influence of an electric field. Electroporation, still another type of electrotransport, involves the passage of an agent through pores formed by applying a high voltage electrical pulse to a membrane. In many instances, more than one of these processes may be occurring simultaneously to a different extent. Accordingly, the term "electrotransport" is given herein its broadest possible interpretation, to include the electrically induced or enhanced transport of at least one charged or uncharged agent, or mixtures thereof, regardless of the specific mechanism or mechanisms by which the agent is actually being transported. Electrotransport delivery generally increases agent delivery and reduces polypeptide degradation during transdermal delivery.

Another method of increasing the agent flux involves pre-treating the skin with, or co-delivering with the beneficial agent, a skin permeation enhancer. A permeation enhancer substance, when applied to a body surface through which the agent is delivered, enhances its flux therethrough such as by increasing the permselectivity and/or permeability of the body surface, reducing the electrical resistance of the body surface to the passage of the agent and/or creating hydrophilic pathways through the body surface in the case of transdermal electrotransport delivery, and/or reducing the degradation of the agent.

There also have been many attempts to mechanically penetrate or disrupt the skin in order to enhance the transdermal flux. See for example, U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97103718, WO 98/11937, WO 98/00193, WO 97/48440, WO 97148441, and WO 97/48442. These devices use piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having dimensions (i.e., a microblade length and width) of only about 25–400 µm and a microblade thickness of only about 5–50 µm. These tiny piercing/cutting elements are meant to make correspondingly small microslits/microcuts in the stratum corneum for enhanced transdermal agent delivery therethrough.

A limitation on devices having such tiny skin penetrating elements is that the elastic properties of the patient's skin 30 allow the skin to conform around the individual skin penetrating elements 32 significantly before those elements actually breach the skin as shown in FIG. 1. In order to overcome this conforming effect and offsetting the condition in which the patient's skin is slack between the penetrating elements 32 as shown in FIG. 2, the skin penetrating elements are sometimes designed to be four to five times longer than what is necessary for the desired penetration depth. The conformance of the skin around the individual skin penetrating elements can also diminish the advantage of a sharp tip on each element because the entire bottom edge of the skin penetrating element is pushed against the skin, as can be seen in FIG. 1. In addition, the tissue layers under the stratum corneum can cause uneven distribution of the total force applied by allowing more conformance around some microprotrusions than others, resulting in several different local pressures across the site. As can be seen in FIG. 2, this results in nonuniform penetration depth across the site by the individual skin penetrating elements which each penetrate the skin to a different depth 35. It is desirable to produce devices for more reliable penetration for producing more uniform flux of an agent being delivered.

DESCRIPTION OF THE INVENTION

The device of the present invention more consistently and reliably penetrates a body surface, e.g., the outermost layer of skin, to enhance agent delivery through 1) greater uniformity of the penetration pattern, 2) deeper penetration with the same size or smaller microprotrusions, and 3) increased size of the resulting pathways. The present invention provides enhanced penetration by controlling the effective mechanical properties of the body surface by reducing the compliance, i.e., extensibility, of the body surface 30. The compliance or extensibility is reduced by applying tension at the application site, i.e., stretching the skin taut, during penetration of the body surface with skin penetrating elements 34 as shown in FIG. 3. Applying tension to the body surface 30 with the device of the present invention reduces the extensibility of the patient's skin, and makes the extensibility more uniform from patient to patient, resulting in reproducibility of penetration from site to site and application to application.

The device of the present invention stretches the patient's skin during penetration by a plurality of microprotrusions. As used herein, the term "microprotrusions" refers to very tiny skin piercing elements, typically having a length of less than 500 µm, a width of less than 400 µm and a thickness of 5 to 100 µm which make correspondingly sized microcuts/microslits in the skin. Upon piercing through the outermost layer (i.e., the stratum corneum) of the skin, the microprotrusions form pathways as shown in FIGS. 3 and 4 through which an agent such as a drug can be introduced, i.e., transdermally delivered. A principal advantage of the present invention is that the device ensures uniform penetration, i.e., generates the same size and depth pathways, by the microprotrusions across the device. Furthermore, the present invention reproducibly provides uniformity in penetration from patient to patient and can form deeper penetrations with shorter microprotrusions.

The device of the present invention uses stretching elements which engage the surface of the skin, such as with adhesive, and create opposing forces across the surface of the skin surface so as to create tension at the skin surface between the skin stretching elements. When piercing the skin with very tiny microprotrusions, the degree of tension under which the skin is placed becomes much more critical compared to skin piercing using substantially larger skin piercing elements such as blood drawing lancets. In accordance with the present invention using microprotrusion piercing, the skin is placed under a tension in the range of about 0.01 to about 10 M Pa, and preferably in the range of about 0.05 to about 2 M Pa (M Pa=megapascal=$1 \times 10^6$ pascals). Thus, the skin stretching/tensioning devices according to the present invention apply a predetermined amount of tension (i.e., stress) in the range from about 0.01 to about 10 M Pa, and preferably in the range of about 0.05 to about 2 M Pa. The amount of skin strain resulting from a given tension varies between individuals depending upon skin characteristics, such as the age of the patient, the location on the patient's body and the tensioning direction. Therefore, in order to adapt to individual characteristics and improve penetration, the skin tensioning devices according to the present invention preferably are designed to provide a given tension (stress) rather than a given strain. In general, for these stress or tension ranges, the applied skin strain is within about 5 to 60% and most preferably within about 10 to 50%. Strain is the amount of skin stretch per unit length of skin and is defined as the change in length of skin in an extended or stretched state divided by the length of skin in a non-stretched state. The strain can be expressed mathematically by the following equation:

$$\text{Strain} = (l_{ext} - l_{non-ext}) \div l_{non-ext}$$

wherein:

$l_{ext}$ is the length of a sample of skin in a stretched state; and $l_{non-ext}$ is the length of the skin sample in a non-stretched state.

With the skin in tension, the skin is less compliant and less extensible, resulting in the microprotrusions being able to pierce the outermost layer of the skin without the skin conforming around or giving way to the microprotrusions so easily. The stretched skin allows nearly complete penetration by all of the microprotrusions, so as to produce a substantial number of agent pathways and electrical continuity (if electrotransport is used) with the skin for continued and reproducible agent flux through the skin. With the skin at the site of application being held taut by the stretching elements the surface of the skin itself is now exerting more resistance to the applied pressure by the points of the microprotrusions. This allows for more reproducible penetration from patient to patient, or from one site to another on a patient, by making the underlying characteristics of the tissue layers under the stratum corneum less influential on penetration as the surface of the skin is exerting resistance to the applied pressure.

In one aspect of the invention, the apparatus comprises an expandable device with skin engaging portions which in use stretches the patient's skin, and a skin penetrating device having a plurality of microprotrusions adapted to pierce the stratum corneum prior to transdermal agent delivery therethrough. One example of a suitable skin penetrating device includes a relatively thin, flexible sheet, which in use is adapted to be placed in substantially parallel relation with the body surface to be pierced. The sheet has a plurality of microprotrusions extending perpendicularly from a body proximal side of the sheet and at least one opening therethrough, which allows the agent to pass between a reservoir associated with the sheet (and typically positioned on the body distal surface of the sheet) and the holes or pathways pierced in the outermost layer of the body surface by the microprotrusions.

The device of the present invention can be used in connection with agent delivery, and in particular, transdermal drug delivery. Delivery devices for use with the present invention include, but are not limited to, electrotransport devices, passive devices, osmotic devices, and pressure-driven devices.

BRIEF DESCRIPTION OF THE DRAWINGS

Many objects and advantages of the present invention will be apparent to those skilled in the art when this specification is read in conjunction with the attached drawings, wherein like reference numerals are applied to like elements, and wherein:

FIG. 29 is a section view of a microblade array having a single row of blades adapted to be dragged across the skin surface;

FIG. 30 is a sectional view of one of the microblades illustrated in FIG. 29, taking along line 130—130;

FIG. 31 is a perspective view of one embodiment of a hand held device which incorporates the microblade array of FIG. 29; and FIG. 32 is a perspective view of the device shown in FIG. 30 after dragging the microblade array across the skin.

MODES FOR CARRYING OUT THE INVENTION

Figure 1:
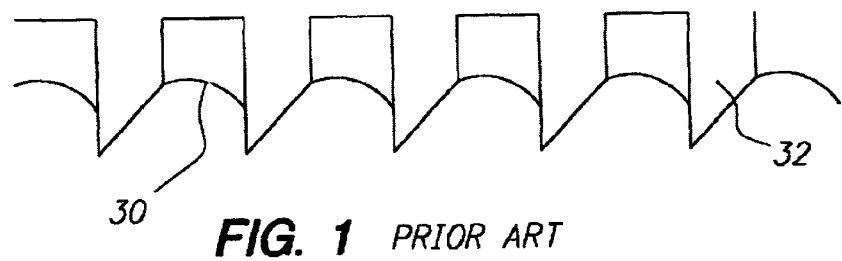
FIG. 1 is an enlarged diagrammatic view of microprotrusions being applied to unstretched skin as was done in the prior art.
Figure 2:
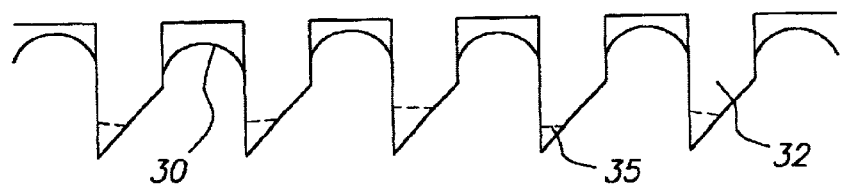
FIG. 2 is an enlarged diagrammatic view of microprotrusions after penetrating unstretched skin as was done in the prior art.
Figure 3:
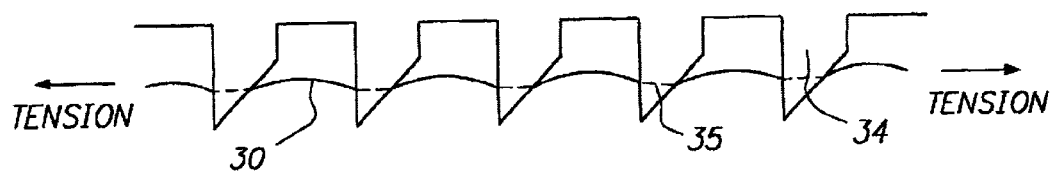
FIG. 3 is an enlarged diagrammatic view of microprotrusions being applied to stretched skin in accordance with the present invention.
Figure 4:
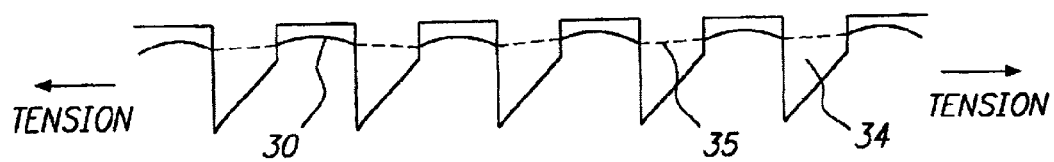
FIG. 4 is an enlarged diagrammatic view of microprotrusions after penetrating stretched skin in accordance with the present invention.

As shown in FIGS. 3 and 4, the present invention comprises stretching the skin 30 during piercing of the skin 30 by microprotrusions 34. The stretching constrains the skin motion (i.e., conformability) relative to the penetrating action of the microprotrusions 34 so as to make the depth of penetration 35 by the microprotrusions 34 into the skin 30 more reliable and uniform.

Figure 17:
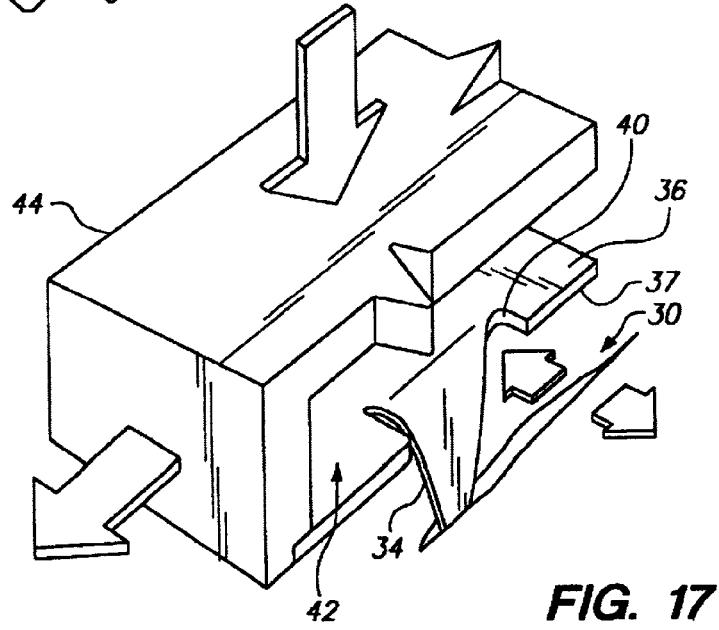
FIG. 17 is an enlarged perspective view of a portion of the device shown in FIGS. 15 and 16.
Figure 20:
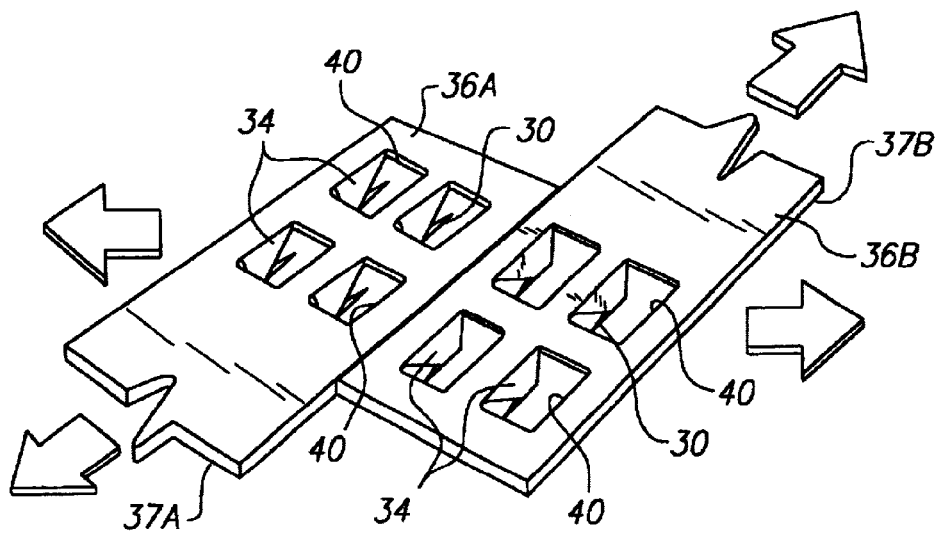
FIG. 20 is an enlarged perspective view of a portion of the device shown in FIGS. 18 and 19.

The present invention involves stretching a body surface (e.g., skin) just prior to and during piercing with the microprotrusions of the aforementioned size to create a plurality of microcuts/microslits therein. The microcuts/microslits can be formed by any suitable body surface penetrating device as the invention is not limited in this respect except with respect to the size of the microprotrusions. Thus, the present invention can be used with many known skin piercing or skin cutting microprotrusions, for example, those described in U.S. Pat. Nos. 5,279,544; 3,964,482; 5,250,023; Reissue 25,637; 5,312,456 and those disclosed in PCT Publication Nos. WO 97/48440, WO 96/37256, WO 97/03718, WO 98/11937, and WO 98/00193, which are incorporated herein by reference in their entirety. One particularly preferred type of microprotrusion device is shown in FIGS. 9, 17 and 20 and is comprised of a plurality of microprotrusions 34 extending outwardly from one surface of a thin, compliant member or sheet 36 with its main surface 37 oriented parallel to the patient's body surface 30.

Figure 24:
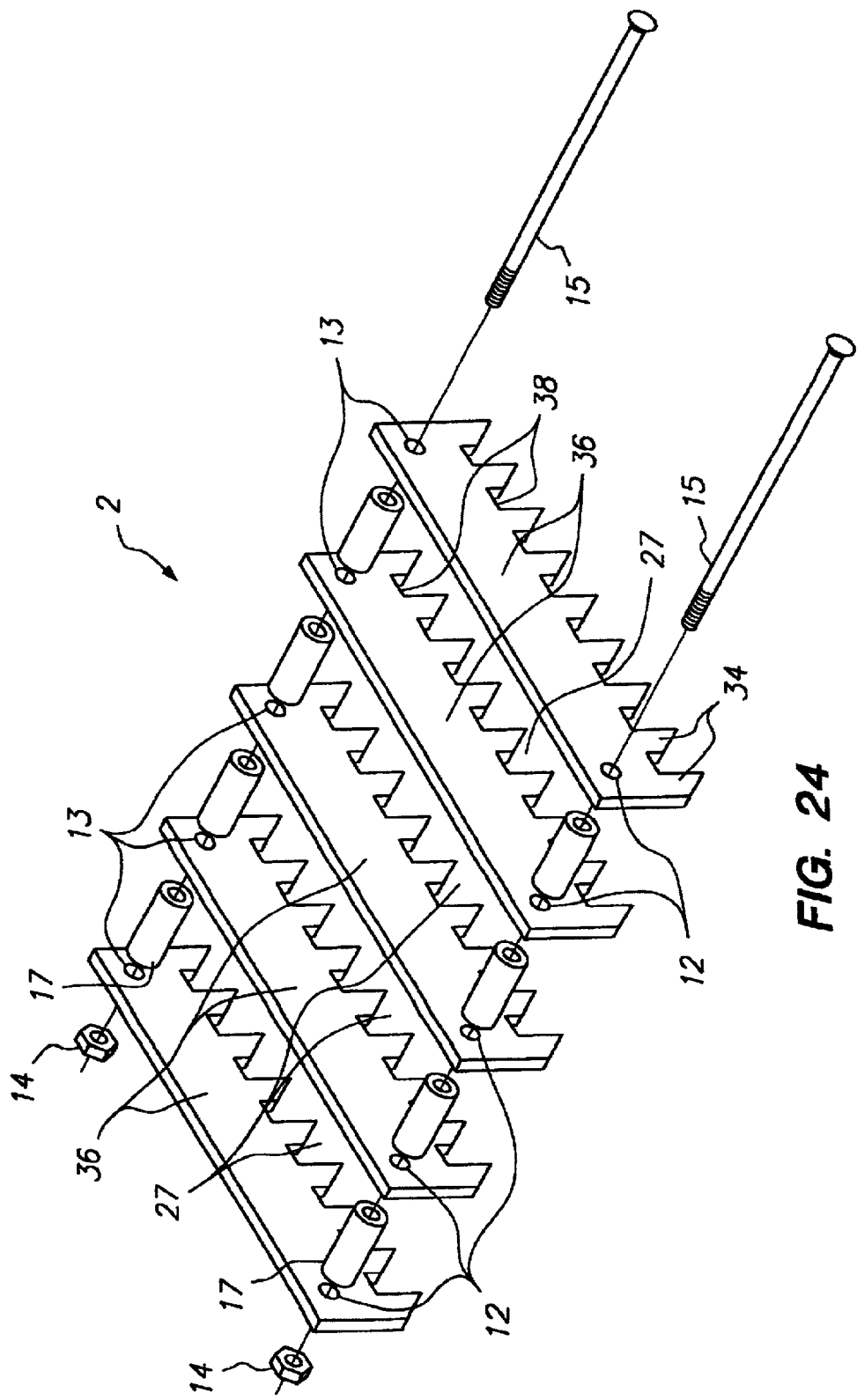
FIG. 24 is an alternate embodiment for the microprotrusions of the present invention.

A particularly preferred configuration for the microprotrusion device is illustrated in FIG. 24 and comprises a plurality of individual sheet members 36 stacked together to form the device 2. Each thin sheet 36 in use is oriented perpendicular to the patient's body surface 30. The sheets 36 each have a plurality of microprotrusions 34 in the same plane as the sheet 36 and which extend outward from a body proximal edge 38 of the sheet 36 for penetrating the body surface 30. Each of the sheet members 36 has a pair of holes 12, 13 through which bolts 15 are inserted. Spacers (e.g., tubes) 17 are positioned between each adjacent pair of sheet members 36 to form voids 27 therebetween. The spaced sheet members 36 are held together as a unit by passing the bolts 15 through the sheet members and spacers 17 and securing nuts 14 on the ends of the bolts, or using other known fasteners. The voids 27 can be filled with a reservoir matrix material (e.g., a gel) adapted to contain the beneficial agent to be delivered. Those skilled in the art will appreciate that spacers 17 having other than tube-like configurations (e.g., square or rectangular blocks) can also be used to provide voids 27 between the agent reservoir 42 (i.e., the agent reservoir contained in the voids 27) and the skin. Furthermore, more than two sets of bolts 15, or other fastening pins, may be used to secure the sheet members 36 and spacers 17 together.

Figure 9:
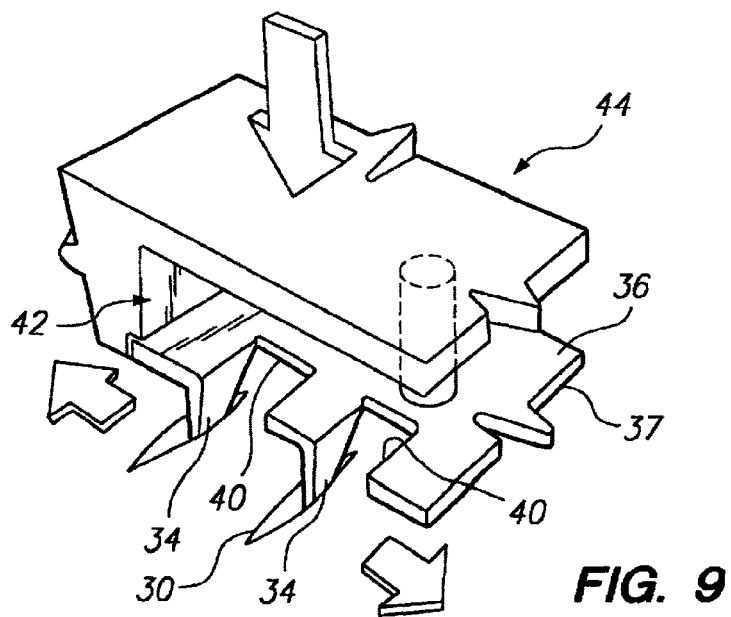
FIG. 9 is an enlarged perspective view of a portion of the device shown in FIGS. 5–8.

In either the FIG. 9 or the FIG. 24 embodiments, the sheet members 36 are generally compliant and flexible because of their relatively thin thickness, for example, about 5 μm to about 100 μm, preferably about 25 μm to about 50 μm.

As used herein, the term "stretching" means applying a tension in the range of about 0.01 to about 10 M Pa, and preferably about 0.05 to about 2 M Pa, to the skin at the time of puncturing the skin with the microprotrusions. As used herein, the term "unilateral stretching" means tensioning the skin in one direction. As used herein, the term "bilateral stretching" means tensioning the skin in two directions. As used herein, the term "shear puncturing" means the microprotrusions are moved parallel to the surface of the skin. As used herein, the term "normal puncturing" means the microprotrusions are moved normal to the surface of the skin. As used herein, the term "longitudinal shearing" means shear loading that is oriented parallel to the direction that the skin is stretched. As used herein, the term "transverse shearing" means shear loading that is oriented orthogonal to the direction that the skin is stretched. As used herein, the term "global puncturing" refers to microprotrusions that all move as a single unit rather than relative to one another during insertion. As used herein, the term "local puncturing" refers to microprotrusions which move relative to one another, usually in opposite directions, during insertion.

Figure 25:
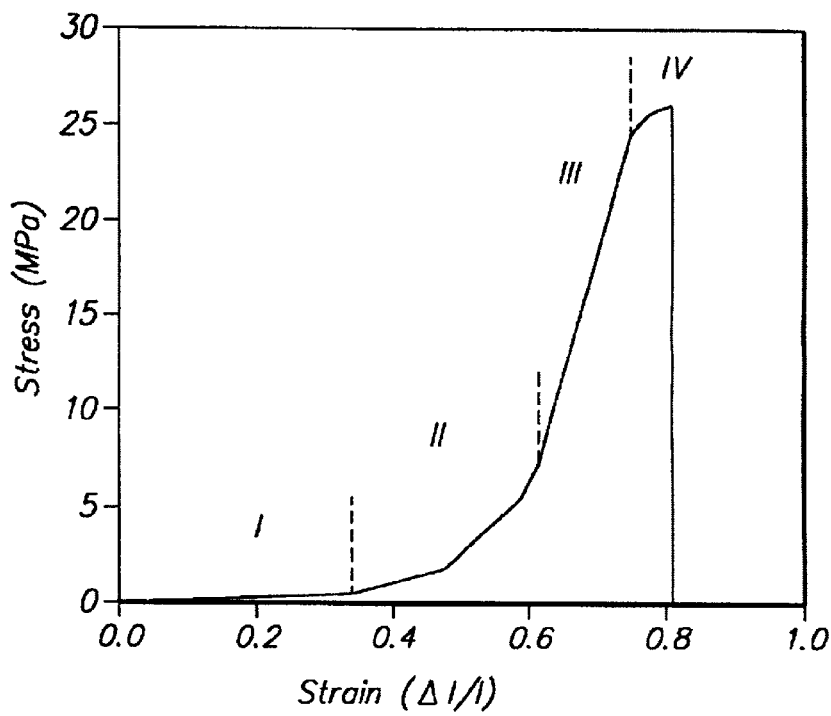
FIG. 25 is a graph of tension or force applied versus skin strain.

FIG. 25 illustrates the typical stress-strain curve for an in vitro tensile test on excised mammalian skin. In phase I there is rapid extension of skin under low load. In phase II there is rapid stiffening of skin followed by phase III in which the skin has stiff behavior. If the skin is tensioned to a degree that reaches phase IV skin tearing and rupture occurs. For effective skin stretching according to the present invention, it is desirable to tension to a degree that results in phase II or III strain, but not phase IV strain. FIG. 25 illustrates the typical stress-strain curve for unpierced skin, however, the curve may vary somewhat for skin which has been pierced by an array of microprotrusions.

The device of the present invention is for use in the percutaneous administration of an agent. The terms "substance", "agent", and "drug" can be used interchangeably and broadly include physiologically or pharmacologically active substances for producing a localized or systemic effect or effects in mammals, including humans and primates, avians, valuable domestic household, sport, or farm animals, or for administering to laboratory animals such as mice, rats, guinea pigs, and the like.

The major barrier properties of the skin, such as resistance to agent permeation, reside with the outermost layer of the skin, i.e., stratum corneum. The inner division, i.e., the underlying layers, of the epidermis generally comprise three layers commonly identified as stratum granulosum, stratum malpighii, and stratum germinativum. There is essentially little or no resistance to transport or to absorption of an agent through these layers. Therefore, for enhancing transdermal flux the microprotrusions used to create pathways in the body surface in accordance with the present invention need only penetrate through the stratum corneum in order for the agent to be transdermally delivered with little or no resistance through the skin.

Figure 8:
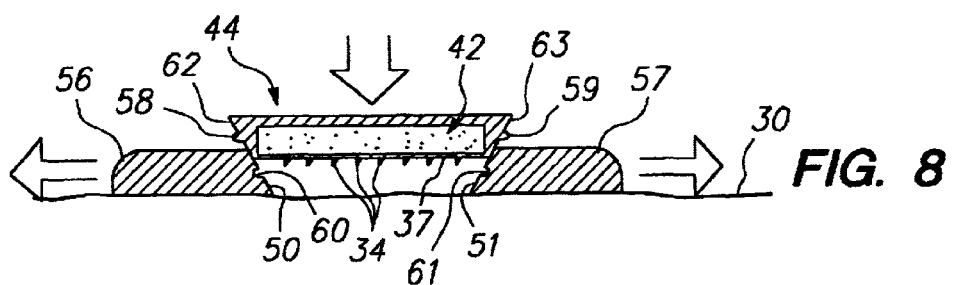
Figure 15:
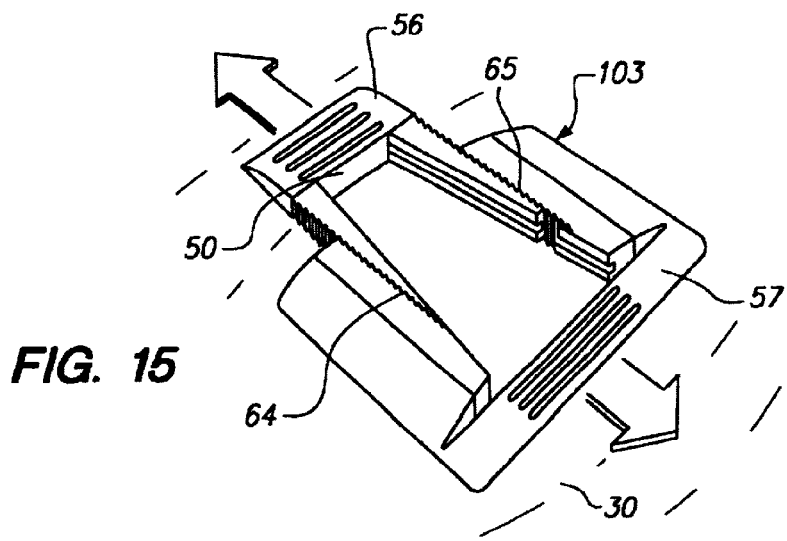
FIGS. 15 and 16 illustrate operation of a fourth device in accordance with the present invention.
Figure 16:
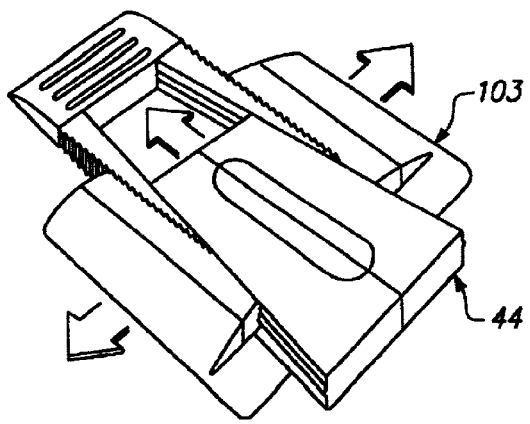

The devices shown in FIGS. 5–12 utilize microprotrusions that pierce the body surface by global, normal puncturing. That is, all of the microprotrusions move as a single unit normal to the skin during the piercing process. With each of these devices, the skin is stretched during puncturing, and the load used to puncture is applied normal to the skin. The stretching of the skin can be transverse to the microprotrusions as shown in FIG. 9, or the array of microprotrusions can be rotated 90° such that the stretching occurs in line with each of the microprotrusions 34 as shown in FIG. 8. After penetration by the plurality of microprotrusions 34, the skin optionally remains under tension created by the skin stretching portions of the devices. Most of the embodiments of the present invention utilize unidirectional stretching of the skin. However, bi-directional stretching can be used as well as shown in FIGS. 15–16. In addition, impact insertion of the microprotrusions may also be employed in any of the embodiments by bringing the microprotrusions into contact with the skin at a predetermined impact velocity which causes the microprotrusions to penetrate the skin.

Figure 5:
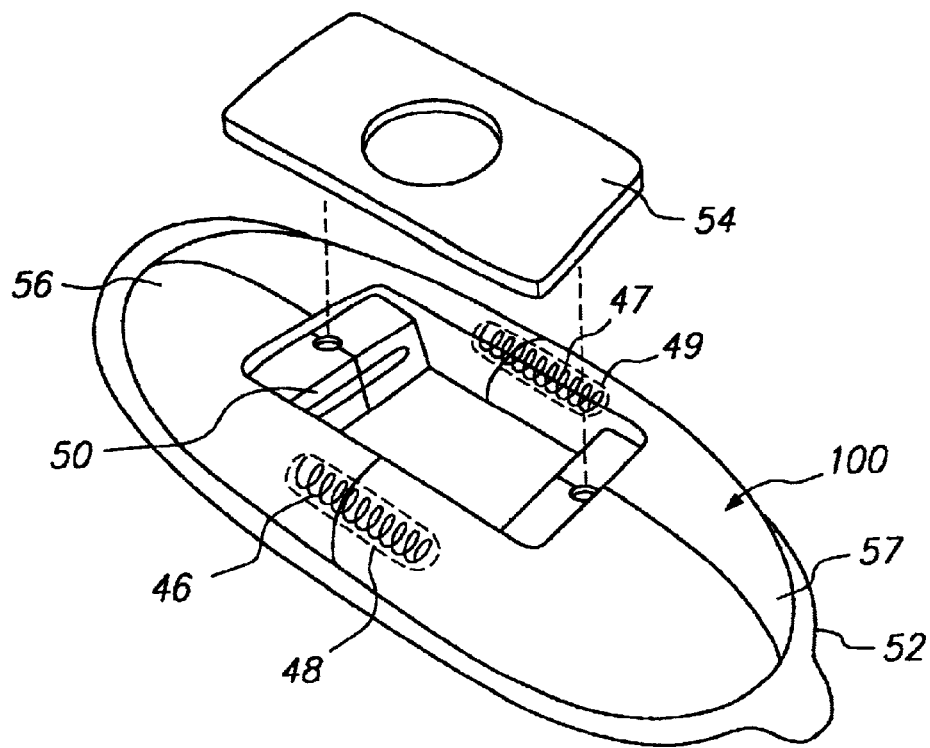
FIG. 5 is a perspective view of a device in accordance with the present invention.
Figure 6:
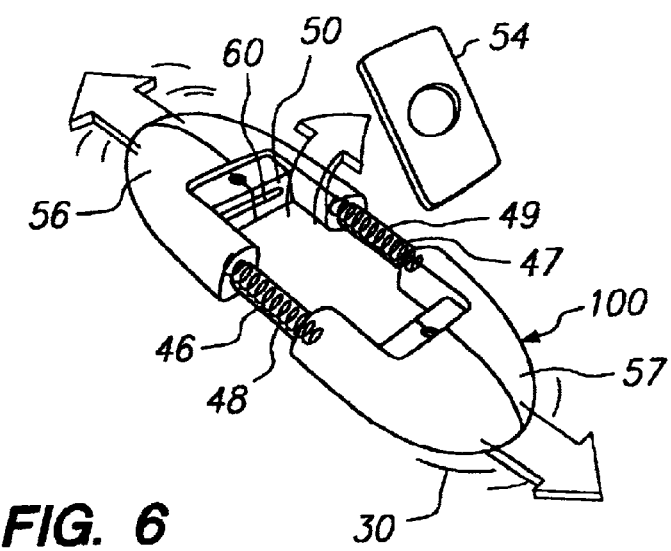
FIGS. 6–8 illustrate operation of the device shown in FIG. 5.
Figure 7:
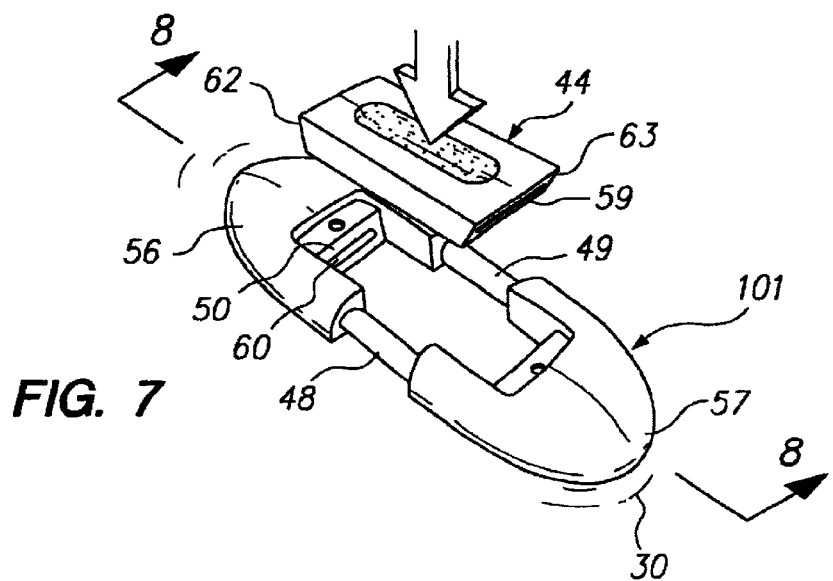

The expandable device 100 shown in FIGS. 5–8 uses biasing members 46 and 47 (e.g., springs) housed in hollow cylindrical members 48 and 49 to initially stretch the body surface, and then biasing members or inclined surfaces 50 and 51 (FIG. 8) or a combination of both to stretch the body surface 30. The expandable device 100 has an adhesive on the skin-contacting surface thereof, initially protected by a release liner 52 (FIG. 5). A disposable retainer 54 holds the opposite ends 56 and 57 of the device together such that the biasing members 46 and 47 located within the device are in compression. The patient removes the release liner 52 and applies the device 100 to a portion of the skin surface 30 such that the adhesive on the skin-contacting surface holds the device to the patient's skin surface 30. Then the disposable retainer 54 is removed from the top of the device 100 to release the biasing members 46 and 47 which are in compression so that the device 100 expands a predetermined distance to stretch the skin in the aforementioned tension range. A snap-in cartridge housing 44 having a microprotrusion array on a skin-engaging surface and a reservoir 42 (FIG. 8) therein is then snapped into the elongated opening left by the expansion of the device 100 such that the protrusions 58 and 59 on each end of the housing 44 lock into the indentations 60 and 61. In an optional embodiment as illustrated, the ends 62 and 63 of the cartridge housing 44 form a wedge to match the inclined surfaces 50 and 51 so that when the cartridge is snapped into the expandable device 100, the opposite ends 56 and 57 stretch the skin even farther. It is also within the scope of the present invention that the surfaces 50 and 51 and ends 62 and 63 are not inclined such that the stretching is done only by the biasing members 46 and 47. As seen in FIG. 9, the stretching of the body surface transverse to the plane of the microprotrusion not only helps with the initial penetration but also holds the pathways through the body surface 30 open during delivery or sampling.

Figure 10:
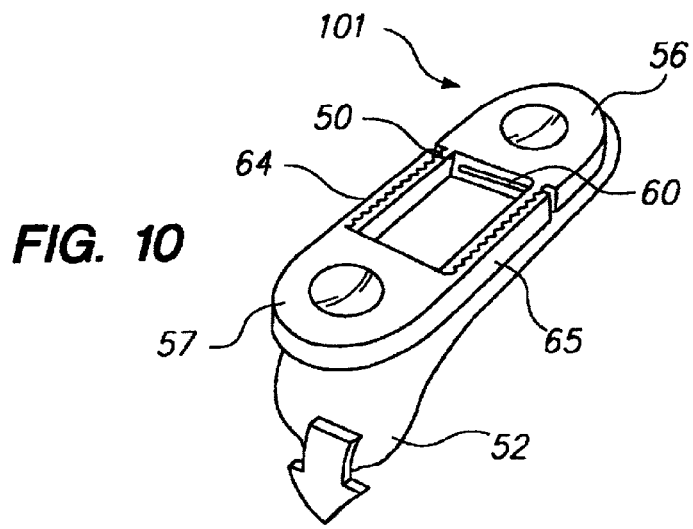
FIGS. 10–12 illustrate operation of a second device in accordance with the present invention.
Figure 11:
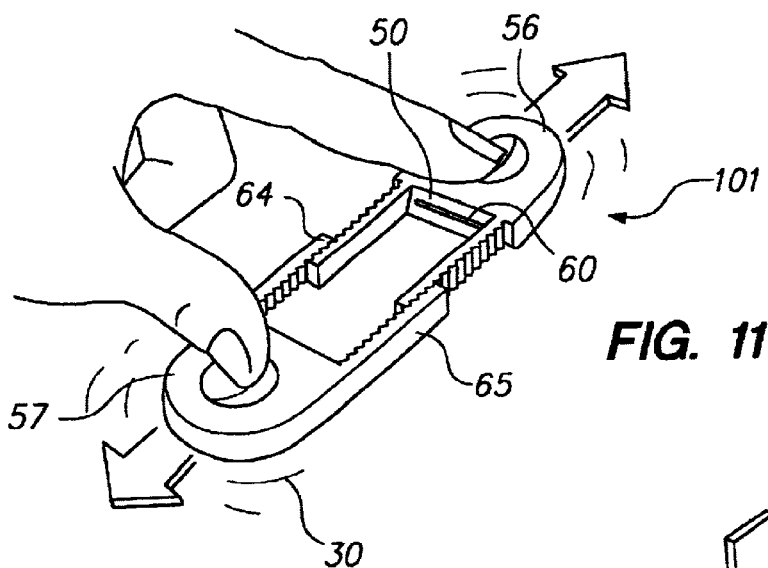
Figure 12:
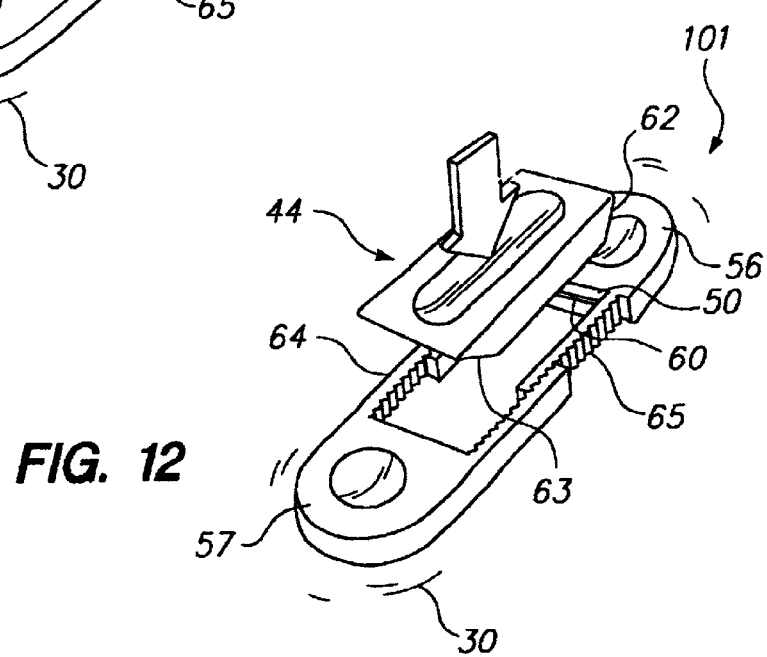

A second embodiment of the invention is illustrated in FIGS. 10, 11, and 12. The expandable device 101 is manually actuated by the patient, but essentially retains the same characteristics of operation as described with respect to device 100, in that the skin is stretched under a predetermined tension in the range of about 0.01 to about 10 M Pa, and preferably about 0.05 to about 2 M Pa, at the time of puncturing and all of the microprotrusions 34 move normal to the skin as a single unit during the insertion process. With respect to this embodiment, the release liner 52 is removed to expose the adhesive on the skin-contacting surfaces of each of the ends 56 and 57 of the device 101, and the device is placed on the patient's body surface. The patient or another person then stretches the skin by spreading apart the ends 56 and 57 of the device as shown in FIG. 11 to a position which provides a skin tension in the range of about 0.01 to about 10 M Pa, and preferably about 0.05 to about 2 M Pa, to improve penetration by the microprotrusions. The ratcheted sides 64 and 65 on the expandable device 101 allow the device to maintain its expanded position after the patient or another has removed their hand from the device. The snap-in cartridge housing 44 is then pressed down with a load applied normal to the body surface 30 as described with respect to device 100, and if the snap-in cartridge housing 44 has the optional wedge shape, then the device 101 will stretch the body surface farther upon insertion of the cartridge housing 44 into the device 101.

Figure 13:
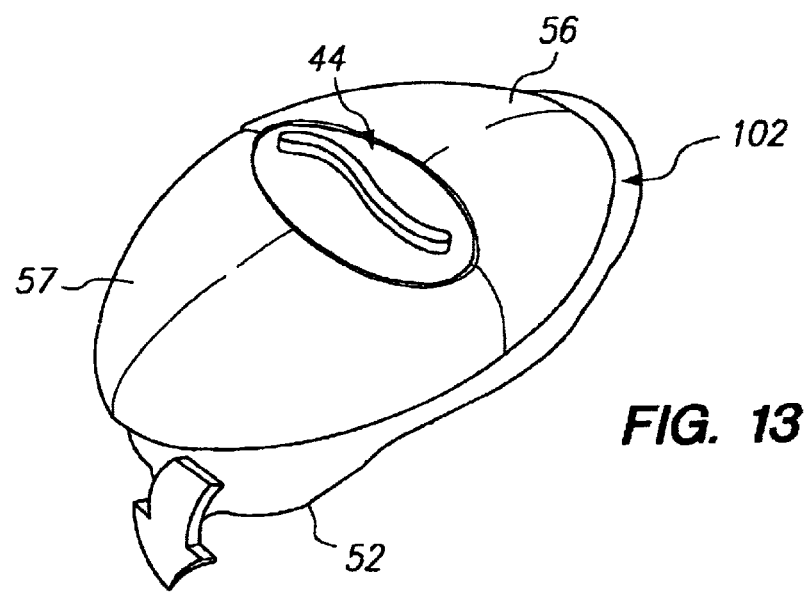
FIGS. 13 and 14 illustrate operation of a third device in accordance with the present invention.
Figure 14:
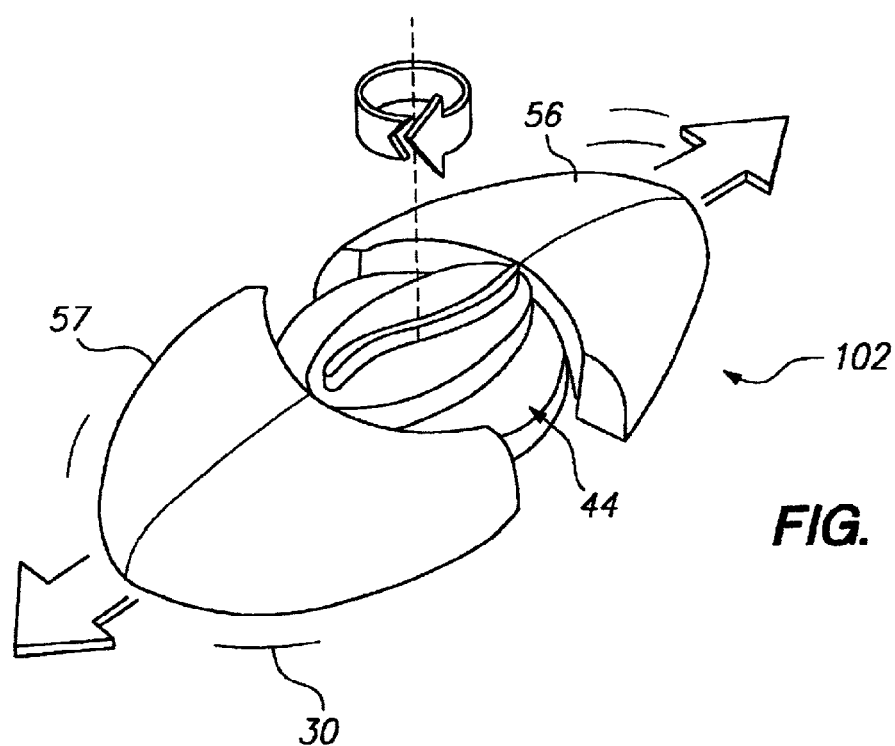

A third embodiment of the invention is illustrated in FIGS. 13 and 14. Device 102 is operated with a rotational motion, rather than a translational motion as illustrated in devices 100 and 101, in order to move the opposing ends 56, 57 of the stretching device 102 a predetermined distance apart which achieves a skin tension in the range of about 0.01 to about 10 M Pa, and preferably about 0.05 to about 2 M Pa. This embodiment of the invention has the entire device 102 as one integral unit, rather than having the agent reservoir and microprotrusion array in a separate cartridge housing 44. The patient or another person removes the release liner 52 from the skin contacting side of the device 102 to expose the adhesive on each end of the device, and places the device 102 on the patient's body surface. The reservoir housing 44 with the microprotrusion array on the underneath side is then rotated, and due to its elliptical shape, forces the ends 56 and 57 of the expandable device 102 apart. The housing 44 is pushed down with a load applied normal to the body surface to have the microprotrusions penetrate the body surface. The housing 44 of the device 102 can also be rotated during or after penetration by the microprotrusions to shear the body surface cutting elongated curved slits.

The fourth embodiment of the invention is illustrated in FIGS. 15–17. Device 103 utilizes global, shear puncturing rather than the global, normal puncturing described with respect to the devices 100, 101 and 102. The global, shear puncturing is movement of all of the microprotrusions 34 in the plane of the skin 30 as a single unit during the insertion process as shown in FIG. 17. According to this embodiment normal pressure is applied before and/or during the movement of the microprotrusions in the plane of the skin to perform shear puncturing.

In addition to shear puncturing, device 103 provides bi-directional stretching of the skin. The skin is stretched in one direction prior to cartridge housing 44 being inserted and in an orthogonal direction when the cartridge housing 44 is inserted. As shown in FIG. 15, similar to those described with respect to device 102, the device 103 is manually actuated by the patient or another, and a ratchet system along each side 64 and 65 holds the skin in the aforementioned tension range for improved skin penetration by the microprotrusions. Then a cartridge housing 44 containing the agent reservoir and a microprotrusion array is slid into the device 100 as shown in FIG. 16 along a direction parallel to the direction of the first tensioning. The cartridge housing 44 has a wedge configuration so that the skin is stretched orthogonal to the original tensioning direction so that the skin is then tensioned along two axes. The microprotrusion array can be oriented so that the plane of the microprotrusions 34 are oriented parallel to the direction that the skin is being stretched to provide longitudinal shearing, or the plane of each of the microprotrusions 34 can be oriented perpendicular to the direction that the skin is being stretched to provide transverse shearing.

In some embodiments of the sheet member 36, the microprotrusions 34 are angled or slanted in the same direction. With this configuration, the cartridge housing 44 can be slid along the body surface in the direction of the slanted microprotrusions while pressing down on the cartridge housing to facilitate better penetration against the elastic nature of the skin.

As one of ordinary skill in the art will recognize, it is also within the scope of the invention that the cartridge housing 44 could be pressed down normal to the plane of the skin with inclined surfaces and ends as described with respect to devices 100, 101, and 102, which would provide bi-directional stretching. In this way, rather than resulting in global, shear puncture as does device 103, it would result in global, normal puncture.

As an alternative, the portion of device 103 illustrated in FIG. 15 can also be used with the hand held device 108 illustrated in FIGS. 29–32. The device 108 can be used to form a plurality of elongated microslits through at least the stratum corneum layer of the portion of the skin held in tension by device 103. In this alternative embodiment, the cartridge housing 44 (FIG. 15) does not have a microprotrusion array on its skin-contacting surface. Device 108 (FIGS. 29–30) is comprised of a head 120 and a handle 122. Mounted in the head 120 is a microprotrusion array 124 which is illustrated in greater detail in FIG. 29. The microprotrsion array 124 is comprised of a plurality of microprotrusions 126 mounted in a plastic member 128. Member 128 has a length substantially greater than its width as best shown in FIGS. 31 and 32 such that the microprotrusions 126 comprise a single row of mircroprotrusions arranged similarly to the tines on a rake. The microprotrusions 126 are preferably formed of a metal and are mounted in the plastic member 128 using known micromolding techniques. Alternatively, the member 128 and the microprotrusions 126 can be one and the same member. For example, the member 128 can be a thin (e.g., 0.03 mm) metal plate having microprotrusions 126 which are photochemically etched and punched as in the processes used to make the microprotrusion arrays shown in FIGS. 9, 17 and 20. The shape of the microprotrusions 126 is not important, although a particularly preferred shape and microprotrsion cross-sectional shape are shown in FIGS. 29 and 30, respectively. In operation, the head 120 of device 108 is placed on the surface of skin 30. As mentioned above, the skin is in a prestretched condition. Thus, for example, the skin can be that portion of the skin 30 which is located in the center of device 103 shown in FIG. 15. The device 108 is then pulled across the surface of the skin in the direction of the arrows shown in FIGS. 29 and 31. This movement causes the microprotrusions 126 to cut through the skin forming a plurality of slits 134 therein. The depth of microprotusion 126 penetration can be controlled by the length of the microprotrusions 126 which typically ranges from 50 to 400 µm. The depth of the microprotrusion 126 cut is controlled by the skin contacting face 132 of member 128 which slides across the surface of skin 30 during the formation of the slits 134.

Figure 18:
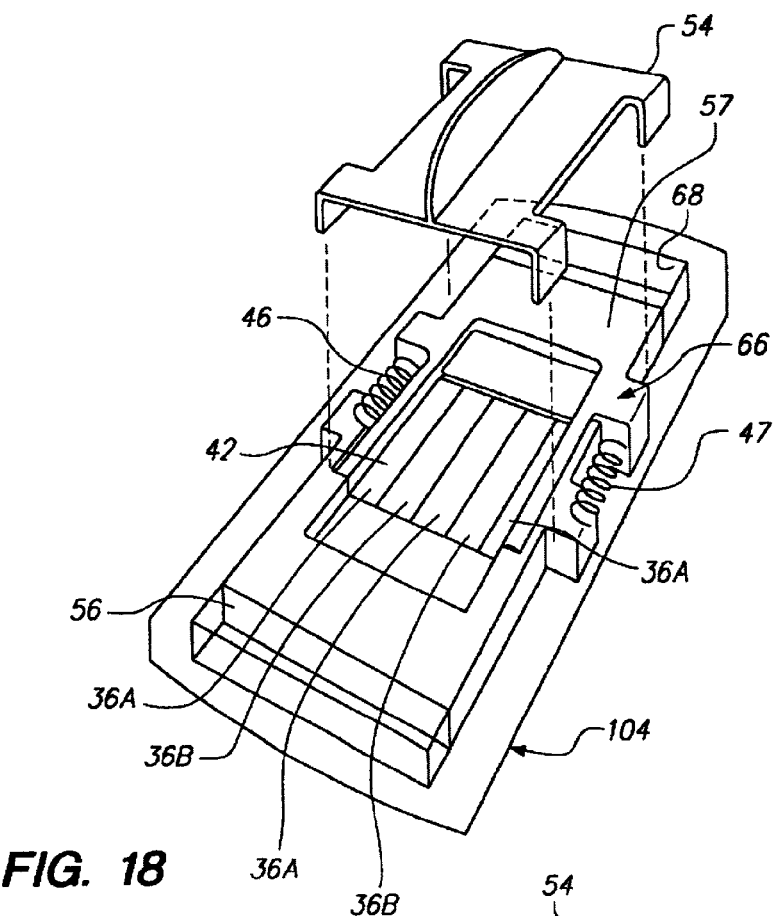
FIG. 18 is a perspective view of a fifth device in accordance with the invention.
Figure 19:
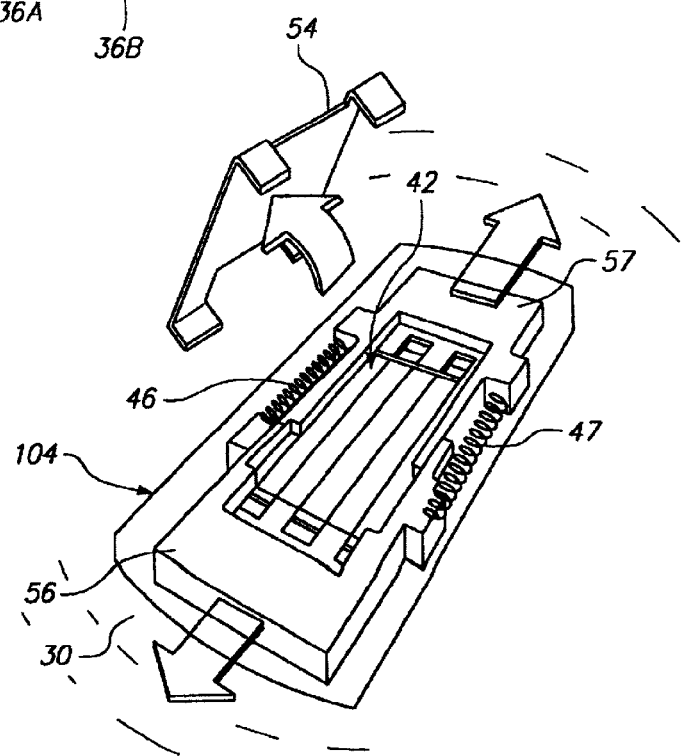
FIG. 19 illustrates the operation of the device shown in FIG. 18.

A fifth embodiment of the invention is illustrated in FIGS. 18–20. The device 104 provides local, shear puncturing. That is, the microprotrusions 34, or small sets of microprotrusions on a plurality of adjacent sheet members 36A and 36B, move in the plane of the skin relative to one another in opposite directions during the insertion process as shown in FIG. 20. The expandable device 104 operates and is constructed essentially the same as device 100. The device 104 initially has biasing members (e.g., springs) 46 and 47 in compression which are held in place by a disposable retainer 54. However, device 104 does differ from device 100 with respect to the microprotrusion array. Device 104 has a plurality of alternating sheet members 36A and 36B sheet members 36A are attached to end 56 of an internal expanding assembly 66 which sits in elongated track 68 of the device. Sheet members 36B are attached to the opposite end 57 of the internal expanding assembly 66. Thus, as assembly 66 is caused to expand due to the biasing members 46 and 47 being released from their compressed state, the alternating sheet members 36A and 36B are pulled over the skin in opposite directions. The device 104 is shown partially in phantom view to show the internal expanding assembly and elongated track 68 more clearly. In addition, the microprotrusion array is already in place in the device 104 prior to removing the disposable retainer 54 rather than being inserted after the stretching. As a result, when the release liner (not shown in FIGS. 18 and 19) is removed from the bottom of the device 104, and the device is adhered to the patient's body surface 30, each of the microprotrusions 34 comes into contact with the patient's skin prior to stretching and continues to contact the skin during stretching. However, due to the elasticity and compliance of the patient's skin, many of the microprotrusions do not puncture or penetrate the body surface initially. Penetration by the microprotrusions does not occur until after the disposable retainer 54 is removed, the skin is stretched a predetermined distance by the ends 56 and 57 of the internal expanding assembly 66 being moved apart by the biasing members 46 and 47, thereby placing the skin under tension in the aforementioned tension range. A force is preferably applied (e.g., by finger pressure) to the skin distal side of device 104, in a direction with a component which is normal to the skin surface so as to force the device 104 against the skin as the skin is being stretched. While the microprotrusions 34 are penetrating the body surface, further separation of the ends 56 and 57 results in the microprotrusions 34 on the sheet members 36A being moved in opposite direction from the microprotrusions 34 on the adjacent sheet members 36B, so as to cause the microprotrusions to shear the body surface as shown in FIG. 20. As one of ordinary skill in the art will appreciate, device 104 can be modified to include alternate (i.e., as an alternative to the disposable retainer 54 and compressed biasing members 46 and 47 of device 104) skin stretching means, such as the ratcheted sides 64, 65 of device 101, the rotatable housing 44 of device 102 or the ratcheted sides 64, 65 in combination with the wedge-shaped housing 44 of device 103.

Figure 21:
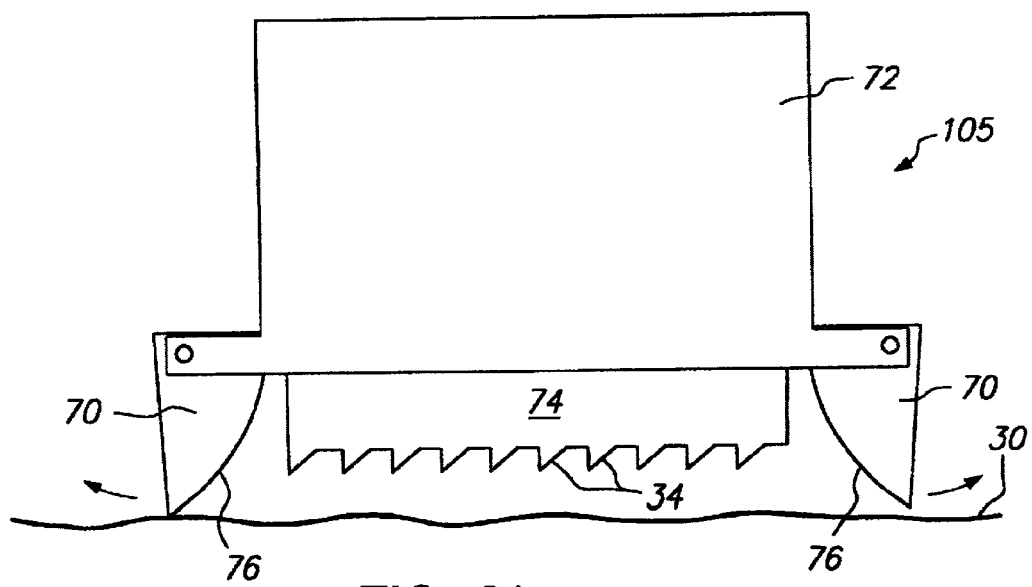
FIG. 21 is a schematic side view of a sixth device in accordance with the present invention.

A sixth embodiment of the invention is illustrated in FIG. 21. The device 105 utilizes rotational members 70 for skin stretching. The skin stretching device 105 includes an upper housing 72 having two or more rotational skin stretching members 70 pivotally mounted thereon. A lower housing 74 containing the agent to be delivered is positioned on a lower surface of the upper housing 72. The lower housing 74 is provided with the plurality of microprotrusions 34 for penetrating the skin surface. Although the device 105 has been illustrated with two rotatable stretching members 70 for unidirectional skin stretching, it should be understood that a plurality of such members can be used for multidirectional skin stretching. As the skin stretching device 105 is pressed onto the skin 30 of the patient, an adhesive on curved surfaces 76 of the rotatable stretching members 70 adheres to the skin on opposite sides of the microprotrusions 34 and pulls the skin 30 apart a predetermined distance, thereby stretching the skin (at a tension within the aforementioned tension range) at the site between the stretching members 70, for improved penetration of the skin 30 by the microprotrusions 34. According to one variation of the device 105, asymmetric shaped stretching members 70 may be used to provide lateral movement for shear puncturing. The microprotrusions 34 of this device may be oriented either parallel to or transverse to the direction of skin stretching.

Figure 22:
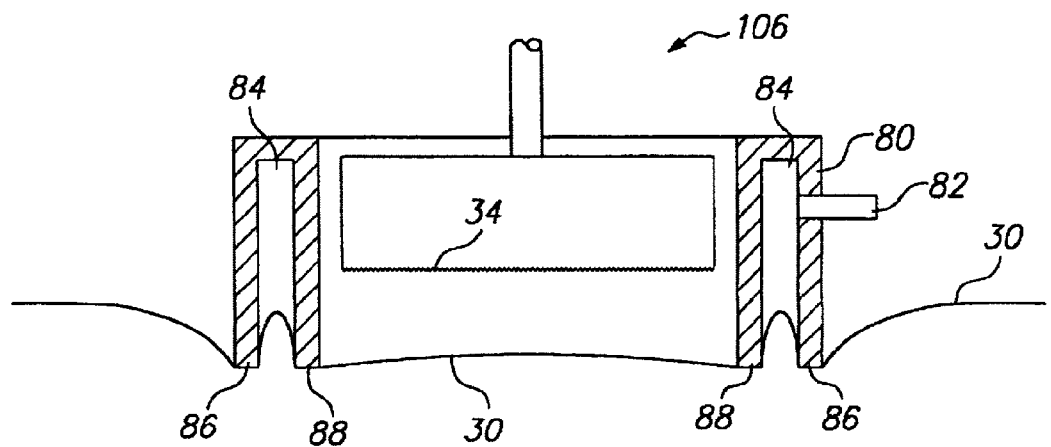
FIG. 22 is a side cross sectional view of a seventh device in accordance with the present invention.

A seventh embodiment of the invention is illustrated in FIG. 22. In this embodiment, the device 106 includes a suction member 80 of a rectangular, square, circular, or other shape in plan view connected to a tube 82 for drawing a suction. The suction member 80 has a suction channel 84. For multi-directional stretching, the suction channel 84 may be a continuous or substantially continuous channel having a rectangular, circular, oval, or other shape in plan view. For unidirectional stretching, two opposed suction channels 84 may be provided. An outer edge of the suction member 80 includes a lower surface 86 which grips the skin by having a high friction coefficient with respect to the skin. A lower surface 88 of an inner edge of the channel 84 is preferably provided with a low friction surface which allows the skin to slide over the surface. The non-slip surface 86 may be an adhesive, while the slip surface 88 may be coated with a lubricant. When a suction is applied to the suction tube 82 a low pressure area is provided within the channel 84 which draws the skin 30 into the channel as shown in FIG. 22, stretching the skin within the opposing surfaces 88. The amount of suction applied within channel 84 will vary depending on the size of device 104. Those persons of ordinary skill in the art can determine the level of suction needed to achieve a skin tension in the range of about 0.01 to about 10 M Pa, and preferably about 0.05 to about 2 M Pa. An array of microprotrusions 34 are then applied to the stretched skin in the center of the device 106.

Figure 23:
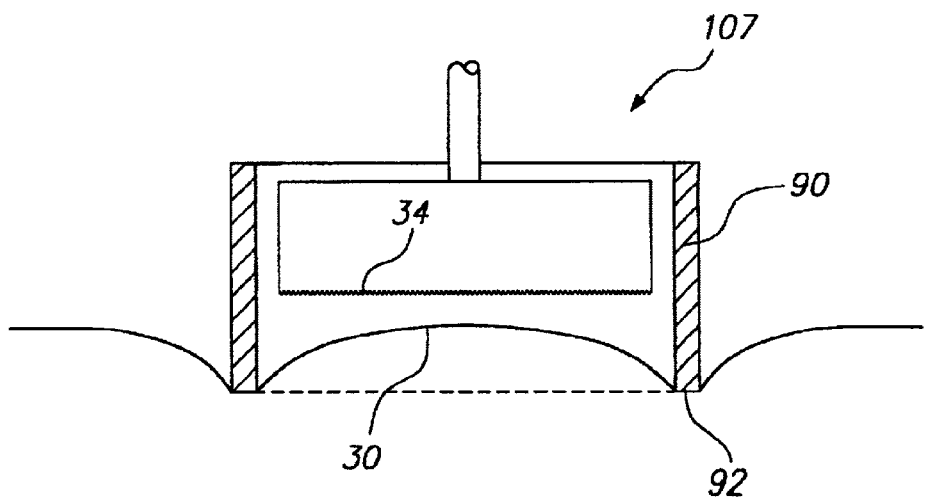
FIG. 23 is a side cross sectional view of an eighth device in accordance with the present invention.

An eighth embodiment of the invention is illustrated in FIG. 23. The device 107 includes a tubular member 90 having a lower, edge 92 which is pressed into the skin surface 30 causing skin in a center of the tubular member to form a dome shape and become tensioned. The amount of skin stretching or tensioning may be controlled by the amount of pressure applied to the tubular member 90. Manually applied pressure is not recommended in this embodiment since the amount of skin tension achieved through manually applied downward pressure applied to member 90 will be variable and hence difficult to ensure a skin tension in the range of about 0.01 to about 10 M Pa. Thus, with this embodiment a device (not shown) for applying a predetermined downward (i.e., toward the skin) force to the tubular member 90 is recommended. To prevent slipage between the skin and the lower edge 92 of the tubular member 90, a non-slip surface, such as an adhesive may be employed. The array of microprotrusions 34 are then applied to the tensioned skin within the tubular member 90. The device 107 as shown in FIG. 23 may be cylindrical, square, rectangular, or any other shape in plan view.

In the preferred embodiments, the microprotrusions 34 are microprotrusions as shown in FIGS. 9, 17, 20, and 22. In the embodiments shown in FIGS. 9, 17, and 20, the sheet member 36 is formed with a plurality of openings 40 adjacent the microprotrusions 34 to permit the transport of agent from an agent reservoir 42 located within housing 44. In this embodiment, the openings 40 correspond to the portion of the sheet member 36 occupied by each of the microprotrusions 34 prior to the microprotrusions being bent into a position which is substantially perpendicular to the plane of the sheet member 36 as shown.

The preferred configurations for the array of microprotrusions and a connecting medium for delivering agents between the reservoir 42 and the body surface are described in detail in WO 97/48440; WO 97/48441; WO 97/48442; and WO 98/28037 which are incorporated herein by reference in their entirety.

The array of microprotrusions 34 in the various embodiments of the present invention may take on different shapes. The present invention can be used with any known delivery device and is not limited to any particular device. It will be appreciated by those working in the field that the present invention can be used in conjunction with a wide variety of electrotransport systems, as the invention is not limited in any way in this regard, see for example electrotransport systems disclosed in U.S. Pat. Nos. 5,147,296; 5,080,646; 5,169,382; 5,423,739; 5,385,543; 5,310,404; and 5,169,383; and PCT Publication No. WO 97/48440, which are incorporated herein by reference in their entirety. Similarly, any known passive transdermal delivery device can be used with the present invention, as the invention is not limited in this regard, see for example passive systems disclosed in U.S. Pat. Nos. 4,379,454; 4,588,580; 4,832,953; 4,698,062; 4,867,982; and 5,268,209; and PCT Publication No. WO 97148440, which are incorporated herein by reference in their entirety. It will be appreciated by those working in the field that the present invention can also be used in conjunction with a wide variety of osmotic and pressure driven systems, as the invention is not limited to a particular device in this regard, for example see U.S. Pat. Nos. 4,340,480; 4,655,766; 4,753,651; 5,279,544; 4,655,766; 5,242,406; and 4,753,651; which are incorporated herein by reference in their entirety.

EXAMPLE 1

To determine the effect of stretching the skin during application of a transdermal delivery device having skin piercing microprotrusions along a skin-contacting surface of the device, the following experiment was performed.

Excised hairless guinea pig skin was pierced, under stretched and unstretched conditions, using a microprotrusion array having a configuration similar to that shown in FIG. 9. The sheet 36 was stainless steel having a thickness of 25 µm. The microprotrusions 34 had a length of 300 µm, a width of 190 µm and were triangularly shaped, with the tip of each microprotrusion having an angle of 35°. The microprotrusion density was 73 microprotrusions/cm$^2$. The stretched samples were manually stretched bi-directionally (↔ and ↕) and pinned on cork. The bi-directional stretching was estimated to achieve a skin tension of between 0.1 and 1 M Pa. The microprotusion array was then applied and removed. The treated sites were then covered with an agent reservoir containing a model drug in the form of a dye. The model drug was comprised of a 1% aqueous solution of methylene blue, with 2% hydroxyethyl cellulose added as a gelling agent to create a hydrogel agent reservoir. The reservoirs were placed on the pierced skin samples and the methylene blue was allowed to passively diffuse from the reservoirs into the skin over a treatment period of 15 minutes. The skin was then tape stripped to remove any dye that still remained on the skin surface. The methylene blue diffused into the microcuts made by the microprotrusions, thereby causing selective staining of the microcuts, making them clearly visible to the eye. Polaroid pictures were taken of each site. These photos showed the length of the microcuts made by the microprojections.

Sample 1: 1 kg/cm$^2$ normal pressure was applied manually for 30 seconds, with no skin stretching.

Sample 2: 1 kg/cm$^2$ normal pressure was applied manually for 30 seconds on manually stretched skin.

The microcuts on sample 1 were smaller than those on sample 2. When the methylene blue was allowed to diffuse in via the microcuts, more dye was found in the larger microcuts of sample 2. This is qualitative data based only on the relative sizes of the dye spots.

EXAMPLE 2

Figure 26:
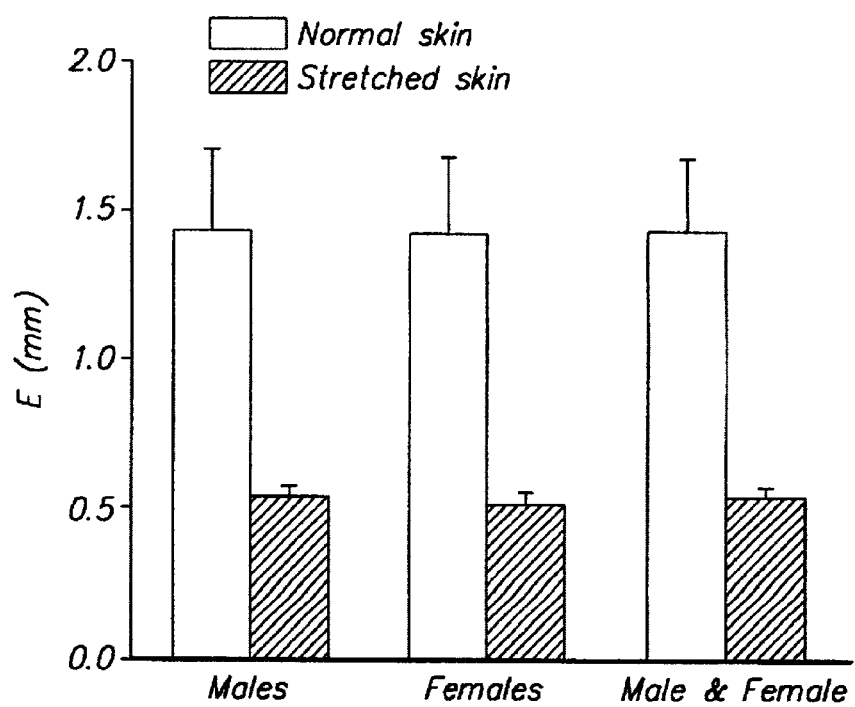
FIG. 26 illustrates the effect of skin stretching on skin extensibility in humans.

Skin Extensibility Evaluation:

Skin extensibility was evaluated in humans using a CUTOMETER SEM 575® (COURAGE+KAHZAKA electronic, GmbH, Koln, Germany) which is conventionally used for measuring skin elasticity in dermatoglogical applications. The CUTOMETER probe (a metal cylinder having a length of about 10 cm, an outside diameter of 3 cm and an inside diameter of 6 mm) was applied on the ventral forearm of four female and four male volunteers ages 26 to 42 years to measure skin extensibility (E). The CUTOMETER applies a negative pressure of 0.5 bar through the inner (6 mm diameter) opening of the probe which is pressed against the skin. The negative pressure causes the skin to be drawn into the probe opening. The CUTOMETER measures the distance the skin is drawn into the probe and provides a skin extensibility (E) measurement in units of distance (mm). Skin extensibility was measured in a normal (i.e., non-stretched) condition as well as under bi-directional (↔ and ↕) manual stretching of the same skin site. The bidirectional stretching was estimated to achieve a skin tension of between 0.1 and 1 M Pa. FIG. 26 shows that similar results were obtained in males and in females. As expected, stretching significantly reduced skin extensibility. Surprisingly, stretching appears to reduce variability of the data as demonstrated by the reduction in the standard deviation values of the data.

Penetration of the microprotrusion array is dependent on the skin physical properties. Reduction of the skin extensibility by stretching indicates that stretching of the skin facilitates penetration of the microprotrusion array for a given force. In addition, it was discovered that stretching of the skin made extensibility of the skin more uniform from subject to subject. This indicates that skin stretching will result in a more uniform application/penetration of the microprotrusion array.

EXAMPLE 3

Effect of Skin Stretching on Transdermal Lisinopril Flux:

The drug lisinopril does not penetrate the skin significantly without the use of penetration enhancers or physical disruption of the skin barrier. In this experiment, lisinopril was delivered by passive diffusion through pathways in the skin created by an array of microprotrusions. The purpose of the experiment was to show that stretching the skin prior to pretreatment with the microprotrusion array improved flux of the drug through the skin in vivo.

In one group of 12 hairless guinea pigs the skin of one flank was stretched manually bi-directionally (↔ and ↕) before application of a foam double adhesive ring having a thickness of 0.8 mm (1/32 inch) with a 2 cm$^2$ hole in the middle which would later contain the drug. The bi-directional stretching was estimated to achieve a skin tension of between 0.1 and 1 M Pa. The adhesive ring served to keep the skin under the drug compartment in the stretched configuration. Next, a 2 cm$^2$ stainless steel microprotrusion array having trapezoidal microprotrusions with microprotrusion lengths of 430 μm and a microprotrusion density of 241 microprotrusions/cm$^2$ was applied to the skin beneath the drug compartment using an approximately 2 kg/cm$^2$ normal manual pressure. The microprotrusion array was held for a few seconds and then removed. A hydrogel containing $^3$H-lisinopril in water (lisinopril 60 mg/mL, pH 5.2, 3% hydroxyethyl cellulose) was dispensed into the drug compartment and a plastic cover was applied to the adhesive outer surface of the ring to seal the system.

Figure 27:
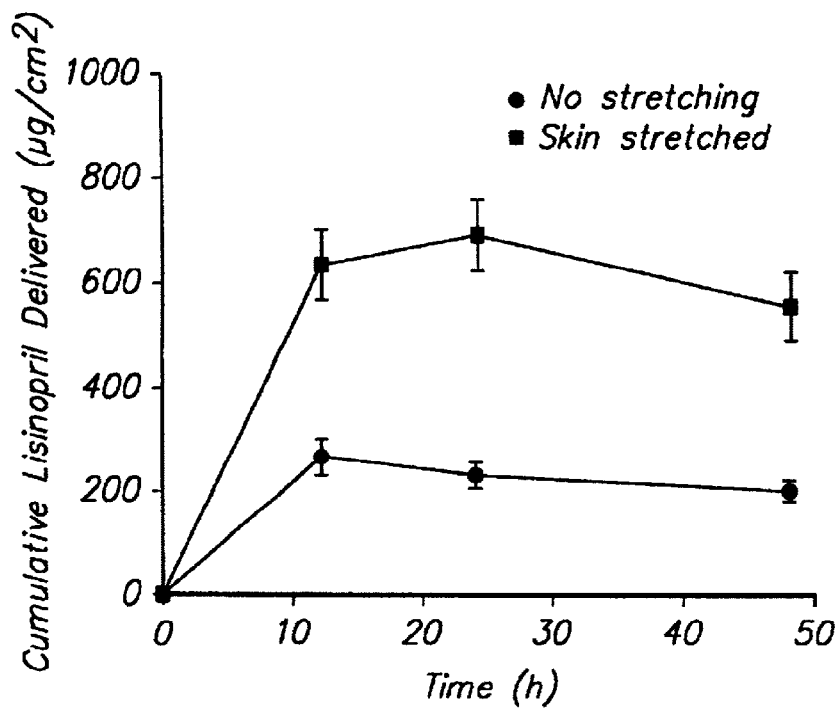
FIG. 27 illustrates the effect of skin stretching on passive lisinopril flux.

A second group of 12 hairless guinea pigs were treated in the same way, except that the skin was not stretched. At 12, 24, and 48 hours after application four systems from each group were removed and residual drug was washed from the skin. The amount of drug penetrated during these time intervals was determined by measuring urinary excretion of tritium (previous studies has shown that in hairless guinea pigs 80% of the tritium derived from $^3$H-lisinopril injected intravenously is excreted in urine). The results shown in FIG. 27, show that penetration of drug during the first twelve hours was significantly enhanced by skin stretching; after 12 hours there was no drug flux in either group. In particular, FIG. 27 shows that the amount of lisinopril delivered transdermally tripled with skin stretching.

EXAMPLE 4

Effect of Skin Stretching on Transdermal Lontophoretic Insulin Flux:

This study examined the effect of skin stretching applied before and maintained during application of a microprotrusion array on the electrically assisted insulin flux in the hairless guinea pig.

Hairless guinea pigs were divided randomly into two groups of four animals. One group of animals received the microprotrusion array delivery system without skin stretching, and the other, received the microprotrusion blade array with skin stretching during application. In the group undergoing skin stretching, the skin of one flank was stretched manually bi-directionally (↔ and ↕) before application of a thin (0.8 mm or 1/32") foam double adhesive ring with a 2 cm$^2$ hole in the middle which would later contain the drug. The bi-directional stretching was estimated to achieve a skin tension of between 0.1 and 1 M Pa. The adhesive ring served to keep the skin under the drug compartment in the stretched configuration. Prior to application of this ring, a 2 cm$^2$ microprotrusion array of stainless steel having trapezoidal microprotrusions with lengths of 430 μm and 241 microprojections/cm$^2$ was attached on the side of the foam contacting the skin across the hole. After application of the ring, an approximately 2 kg/cm$^2$ normal manual pressure was applied on the microprotrusion array and held for a few seconds.

A hydrogel containing Humilin R-500 (Eli Lilly, Indianapolis, Ind.) supplemented with a final concentration of 25 mM L-histidine (base) and 2% (w/v) hydroxyethyl cellulose, was dispensed into the drug compartment. The remainder of the iontophoretic system was added to this construction. The drug-containing formulation was separated from the cathode electrode by a Nafion ion exchange membrane. A gel containing 0.15 M sodium chloride was placed between the cathode and the ionic exchange membrane. The system also comprised an anode compartment which comprised a skincontacting gel containing a saline hydrogel and an anode electrode. The current was preset to 100 µA/cm$^2$. The system was maintained on the animal skin for 2 hours. Blood samples were also collected at 0.5, 1, 2, 3, and 4 hours after system removal. Plasma was then prepared from these blood samples and insulin was analyzed by radioimmunoassay.

Figure 28:
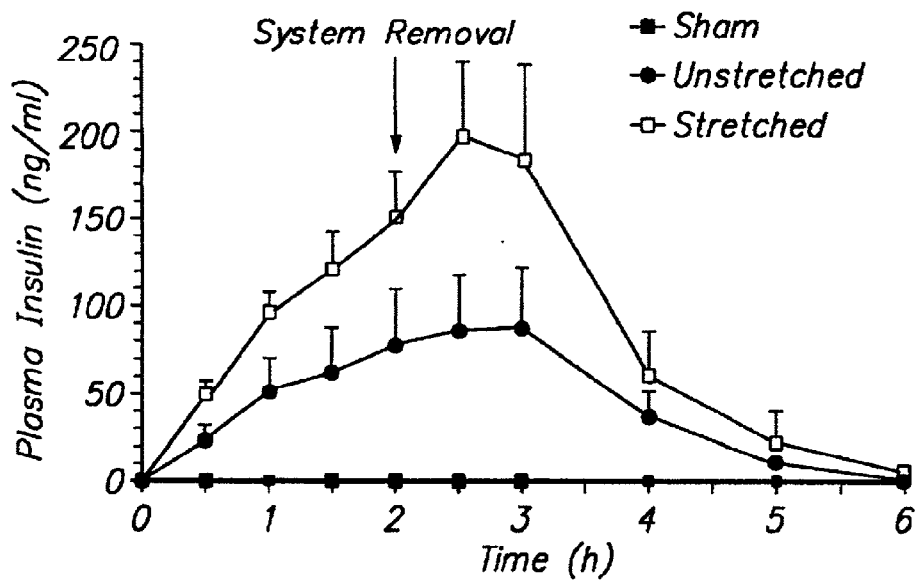
FIG. 28 illustrates the effect of skin stretching on electrically assisted insulin flux.

The results shown in FIG. 28, show a significant enhancement effect of skin stretching on plasma insulin concentrations found in the blood samples. As can be seen in FIG. 28, the skin stretching doubled the amount of insulin delivered trandermally. The average flux (mean±sem) extrapolated from these data using pharmacokinetic analysis was 26±9 µg/cm$^2$h in the unstretched group, versus 53±13 µg/cm$^2$h in the stretched group.

EXAMPLE 5

Effect of Skin Stretching on Microprotrusion Penetration Depth:

This experiment measured the effect of skin stretching on microprotrusion penetration depth using excised hairless guinea pig skin. Two hairless guinea pigs were used in the experiment. Before sacrifice, the skin extensibility (E) of each of the animals was measured using the CUTOMETER described in Example 2. A CUTOMETER probe having an inside diameter of 8 mm was used to measure skin extensibility in this experiment. Six measurements were taken on each side of the animals; three in a natural (i.e., non-stretched) condition and three using manual bi-directional (↔ and ↕) stretching. The bi-directional stretching was estimated to achieve a skin tension of between 0.1 and 1 M Pa. The measured skin extensibilities for non-stretched skin on the live guinea pigs ranged from 2.5 to 3.0 mm while the skin extensibility measurements for the stretched skin ranged from 1.5 to 2.0 mm.

Following these measurements, the animals were sacrificed and skinned from the neck through hind leg region using a scalpel blade. Excess fat under the skin was then removed. The skins were then cleaned with isopropyl alcohol swabs and dried with gauze. The excised skins were then placed over a thin silicone sheet (thickness of 0.3 cm) mounted over a thin piece (thickness of 0.3 cm) of cork board. The excised skins were placed over the silicone and stapled along their perimeter to secure the skins thereto. Skin extensibility measurements were taken with the CUTOMETER and the skin stretch was adjusted (i.e., by removing staples and then restapling) in order to match the extensibility measurements of the live animals. Once the mounted skins had extensibility measurements which matched those of the live animal, the skin tension was assumed to be the same as that achieved through bi-directional stretching of the live animal's skin, and experiments were conducted to measure microprotrusion penetration depth. The microprotrusions used in the experiment were in the form of the metal sheet having a thickness of 0.025 mm (1 mil) having a multiplicity of openings (190 openings/cm$^2$), each opening having one trapezoidally shaped microblade bent at an angle of about 90° to the surface of the sheet. The microprotrusion arrays had a skin-contact area of 2 cm$^2$ and had several shapes, materials, and configurations. The microprotrusion arrays were made from both stainless steel and titanium. The arrays included blade widths of 140 microns and 280 microns. The leading angle of the blade tips were 35° and 55°. Blade lengths ranged between 435 and 486 microns. The skin samples were pierced by mounting the microprotrusion arrays on the head of a spring-loaded impactor which drove the microprotrusion arrays into the skin. In spite of the variety of microprotrusion parameters and impact speeds, the experiments were run such that the non-stretched skin samples were tested using the same variety and number of microprotrusion arrays and impact speeds as the stretched skin samples. Thus, any influence in microprotrusion design, blade width, tip angle, microprotrusion materials and impact speed was eliminated from the study results.

After impact penetration by the microprotrusion array, the skin site was rubbed with india ink both horizontally and vertically for about 15 seconds. Thereafter, the site was cleaned with gauze and water until the surface ink was removed. Each treatment site was then labeled and photographed in order to determine the amount of microslits across the impacted site and the number of microslits/cm$^2$.

The skin samples were then wrapped in foil and sealed in a plastic bag and placed in a freezer overnight. Upon removal from the freezer, three 6 mm cryotomed biopsies were taken from each skin site. The slices were placed on a glass slide in order of increasing depth. When the cryotoming was completed, the india ink stains in each slice were counted at each depth and recorded to determine the penetration of the projections at each depth. The photographs taken prior to cryotoming were used to count the number of penetrations at the surface of each of the sites. For each biopsy, the number of projections that penetrated to, but not yet beyond, each slice was calculated. This data was used to determine mean microprotrusion penetration depths, which are as follows:

Non-stretched mean penetration depth: 54 microns.
Stretched mean penetration depth: 85 microns.

Thus, stretching the skin increased the mean microprotrusion penetration by 57%.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention as indicated by the appended claims rather than the foregoing description, and all changes which come within the meaning and range of equivalence thereof are intended to be embraced therein.

What is claimed is:

1. A method for delivering an agent through a body surface, comprising:
    providing expandable device having a body surface engaging first portion and a body surface engaging second portion;
    contacting the body surface with said expandable device;
    expanding said device to stretch the body surface whereby a tension in the range of about 0.01 to about 10 M Pa is applied to the body surface;
    penetrating said tensioned body surface with a plurality of microprotrusions; and
    delivering an agent through said penetrated body surface.

2. The method of claim 1, wherein a tension in the range of about 0.05 to about 2 M Pa is applied to the body surface.

3. The method of claim 1, further comprising expanding said expandable device by inserting a wedge-shaped housing that contacts surfaces on said first portion and said second portion.

4. The method of claim 1, further comprising expanding said expandable device further by rotating said housing in a space disposed between said first portion and said second portion of said expandable device.

5. The method of claim 1, further comprising removing a retainer that initially holds said first portion and said second portion in a first position so that a biasing member in said expandable device urges said first portion away from said second portion when said retainer is removed.

6. The method of claim 1, further comprising holding said expandable device in said expanded state after said expandable device has been expanded.

7. The method of claim 6, wherein said expandable device is held in said expanded state in a first direction and said method further comprises expanding said expandable device in a second direction.

8. The method of claim 1, including the step of moving said plurality of microprotrusions over the body surface to form a plurality of elongated silts therein.

9. A method for transdermal agent delivery, comprising:
providing an expandable device;
contacting the body surface with said expandable device;
stretching the surface of a patient's skin by expanding said expandable device, said expandable device applying a tension of about 0.01 to about 10 M Pa to the skin;
holding the skin in said stretched condition;
penetrating said stretched skin with a microprotrusion array to form pathways; and
delivering an agent transdermally through the skin via said pathways.

10. The method of claim 9, wherein a tension of about 0.05 M Pa to about 2 M Pa is applied to the skin.

11. The method of claim 9, wherein the skin is stretched in the range of about 5 to 60%.

12. The method of claim 9, including the step of moving said plurality of microprotrusions over the body surface to form a plurality of elongated slits therein.

* * * * *